United States Patent
Brown

(10) Patent No.: US 10,448,957 B2
(45) Date of Patent: Oct. 22, 2019

(54) ADJUSTABLE CUT BLOCK AND SIZER INSTRUMENT FOR ARTHROPLASTY PLANNING

(71) Applicant: Zimmer, Inc., Warsaw, IN (US)

(72) Inventor: David Brown, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 338 days.

(21) Appl. No.: 15/343,765

(22) Filed: Nov. 4, 2016

(65) Prior Publication Data

US 2017/0128079 A1    May 11, 2017

Related U.S. Application Data

(60) Provisional application No. 62/251,944, filed on Nov. 6, 2015.

(51) Int. Cl.
*A61B 17/15*    (2006.01)

(52) U.S. Cl.
CPC .................. *A61B 17/155* (2013.01)

(58) Field of Classification Search
CPC ...... A61B 17/15; A61B 17/154; A61B 17/155
See application file for complete search history.

(56) References Cited

U.S. PATENT DOCUMENTS

| | | | |
|---|---|---|---|
| 5,749,876 A * | 5/1998 | Duvillier | A61B 17/155 606/86 R |
| 7,572,262 B1 | 8/2009 | Hoeppner et al. | |
| 9,005,207 B2 * | 4/2015 | Dodds | A61B 17/155 606/87 |
| 9,050,197 B2 * | 6/2015 | Lorio | A61F 2/4657 |
| 2004/0260301 A1 * | 12/2004 | Lionberger | A61B 17/155 606/88 |
| 2006/0142774 A1 | 6/2006 | Metzger | |
| 2010/0241126 A1 * | 9/2010 | Ghijselings | A61B 17/025 606/88 |
| 2011/0245835 A1 * | 10/2011 | Dodds | A61B 17/155 606/87 |
| 2013/0204259 A1 * | 8/2013 | Zajac | A61B 17/154 606/88 |
| 2013/0325014 A1 * | 12/2013 | Sordelet | A61B 17/155 606/82 |
| 2015/0238202 A1 * | 8/2015 | Collins | A61B 17/155 606/88 |

(Continued)

FOREIGN PATENT DOCUMENTS

| | | |
|---|---|---|
| TW | M495826 | 2/2015 |
| WO | 2017079562 | 5/2017 |

OTHER PUBLICATIONS

"European Application Serial No. 16809563.6, Response filed Jan. 21, 2019 to Office Action dated Jul. 19, 2018", 18 pgs.

(Continued)

*Primary Examiner* — Eric S Gibson
(74) *Attorney, Agent, or Firm* — Schwegman Lundberg & Woessner, P.A.

(57) ABSTRACT

An integrated instrument for arthroplasty planning comprises a cutting block having an adjustable distance between an anterior cut guide and a posterior cut guide, and a sizer mounted to the cutting block, the sizer comprising medial and lateral posterior feet having an adjustable distance from one of the cut guides and an adjustable angular position relative to the one of the cut guides.

18 Claims, 10 Drawing Sheets

(56) References Cited

U.S. PATENT DOCUMENTS

| | | | | |
|---|---|---|---|---|
| 2016/0030053 A1* | 2/2016 | Yager | .................... | A61B 17/155 |
| | | | | 606/88 |
| 2016/0089167 A1* | 3/2016 | Lin | ...................... | A61B 17/155 |
| | | | | 606/88 |
| 2016/0199134 A1* | 7/2016 | Brown | .................... | A61B 19/50 |
| | | | | 703/1 |
| 2017/0100132 A1* | 4/2017 | Collazo | .................. | A61B 17/15 |
| 2017/0128079 A1* | 5/2017 | Brown | ................. | A61B 17/155 |

OTHER PUBLICATIONS

"International Application Serial No. PCT/US2016/060536, Written Opinion dated Feb. 10, 2017", 7 pgs.

"International Application Serial No. PCT/US2016/060536, International Search Report dated Feb. 10, 2017", 5 pgs.

* cited by examiner

ADJUSTABLE CUT BLOCK AND SIZER INSTRUMENT FOR ARTHROPLASTY PLANNING

CLAIM OF PRIORITY

This application claims the benefit of U.S. Provisional Patent Application Ser. No. 62/251,944, filed on Nov. 6, 2015, the benefit of priority of which is claimed hereby, and which is incorporated by reference herein in its entirety.

FIELD

The present subject matter relates to orthopedic systems and specifically to surgical devices for facilitating measuring and cutting of bones during arthroplasty procedures.

BACKGROUND

Revision knee surgery can involve making several measurements and cuts on a bone intraoperatively. It is therefore highly desirable that the measurements and cuts be accurate and precise in order to ensure that an orthopedic implant restores the joint to a functioning state similarly to that of the natural joint. Several devices are available to facilitate the measuring and cutting.

During knee arthroplasty various sizing, balancing and trialing procedures are performed before an implant is selected and/or implanted. For example, the femoral component is carefully sized and the anterior-posterior dimension of the resected distal femur is determined using an anterior-posterior (AP) sizer. Additionally, knee balancing is performed to achieve equal flexion gaps and proper tension of the medial and lateral ligaments using a knee tensor or balancer.

After sizing and the implant is selected, the distal end of the femur is prepared for the implant, such as by resecting various portions of the condyles. Malposition of the joint line is a common complication of revision knee surgery. Various known instruments can be used to reference the natural joint line of the average knee using approximate referencing landmarks. These landmarks include, for example, the inferior pole of the patella, the fibular head, and the epicondyles.

An example sizing and balancing instrument is described in U.S. Pat. No. 9,050,197 to Lorio et al. An example cutting guide instrument is described in U.S. Pat. No. 7,572,262 to Hoeppner et al.

OVERVIEW

An adjustable cut block and sizer instrument for arthroplasty planning is described that facilitates sizing and cutting of bones during a procedure.

To further illustrate the components and methods disclosed herein, a non-limiting list of examples is provided here:

In Example 1, an integrated instrument for arthroplasty planning comprises: a cutting block having an adjustable distance between an anterior cut guide and a posterior cut guide; and a sizer mounted to the cutting block, the sizer comprising: medial and lateral posterior feet having an adjustable distance from one of the cut guides and an adjustable angular position relative to the one of the cut guides.

Example 2 can include, or can optionally be combined with the subject matter of Example 1, to optionally include an anterior cut guide and posterior cut guide that are coupled together at an adjustable post.

Example 3 can include, or can optionally be combined with the subject matter of Example 2, to optionally include a first adjuster knob connected to the adjustable post to change the adjustable distance between the anterior cut guide and the posterior cut guide.

Example 4 can include, or can optionally be combined with the subject matter of Examples 2 and 3, to optionally include an adjustable post that comprises: first and second posts connected to the anterior cut guide and the posterior cut guide, respectively, and telescopically connected to each other; and first and second fingers extending from the first and second posts, respectively; wherein the first and second fingers are coupled to the first adjuster knob to push and pull the first and second posts away from and toward each other.

Example 5 can include, or can optionally be combined with the subject matter of Examples 2, 3 and 4, to optionally include a chamfer block mounted to the adjustable post, the chamfer block comprising: an anterior chamfer cut guide; and a posterior chamfer cut guide; wherein the first adjuster knob additionally adjusts a distance of the chamfer block from the anterior and posterior cut guides.

Example 6 can include, or can optionally be combined with the subject matter of Examples 1, 2, 3, 4 and 5, to optionally include a sizer that is mounted to the cutting block via a pair of shims inserted into one of the cut guides.

Example 7 can include, or can optionally be combined with the subject matter of Examples 1, 2, 3, 4, 5 and 6, to optionally include a shim body having the pair of shims.

Example 8 can include, or can optionally be combined with the subject matter of Example 7, to optionally include a foot body connecting the medial and lateral posterior feet, the foot body being connected to the shim body via an adjuster body.

Example 9 can include, or can optionally be combined with the subject matter of Example 8, to optionally include an adjuster body that is slidably connected to the shim body at a slide pin and pivotably connected to the foot body at a pivot point.

Example 10 can include, or can optionally be combined with the subject matter of Example 9, to optionally include a second adjuster knob coupled to the sizer to adjust an anterior-posterior distance between the foot body and the shim body along the slide pin; and a third adjuster knob coupled to the sizer to adjust an angle between the foot body and the shim body.

In Example 11, an integrated instrument for arthroplasty planning comprises: a cutting guide comprising: an anterior cut guide; a posterior cut guide spaced from the anterior cut guide via an adjustable post; and a first adjuster connecting the anterior and posterior cut guides to adjust a space between the anterior and posterior cut guides at the adjustable post; and an anterior-posterior sizer connected to the cutting guide assembly, the anterior-posterior sizer comprising: a shim body having medial and lateral shims; a foot body having medial and lateral posterior feet disposed adjacent the medial and lateral shims, respectively; an adjuster body connecting the shim body and the foot body via a pivot point and a slide pin; a first adjuster for adjusting the medial and lateral posterior feet relative to each other at the slide pin; and a second adjuster for adjusting the medial and lateral posterior feet relative to each other at the pivot point.

Example 12 can include, or can optionally be combined with the subject matter of Example 11, to optionally include an adjustable post that comprises: first and second posts connected to the anterior cut guide and the posterior cut guide, respectively, and telescopically connected to each other; and first and second fingers extending from the first and second posts, respectively; wherein the first and second fingers are coupled to the first adjuster to push and pull the first and second posts away from and toward each other.

Example 13 can include, or can optionally be combined with the subject matter of Examples 11 and 12, to optionally include a chamfer block mounted to the adjustable post, the chamfer block comprising: an anterior chamfer cut guide slot; and a posterior chamfer cut guide slot; wherein the first adjuster additionally adjusts a distance of the chamfer block from the anterior and posterior cut guides.

Example 14 can include, or can optionally be combined with the subject matter of Examples 11, 12 and 13, to optionally include a second adjuster knob coupled to the sizer to adjust an anterior-posterior distance between the foot body and the shim body along the slide pin; and a third adjuster knob coupled to the sizer to adjust an angle between the foot body and the shim body.

Example 15 can include, or can optionally be combined with the subject matter of Examples 11, 12, 13 and 14, to optionally include an anterior cut guide and posterior cut guide that are disposed parallel to each other perpendicular to the adjustable post; the medial and lateral tabs are disposed in a first plane positioned within the posterior cut guide; and the medial and lateral feet posterior feet are disposed in a second plane spaced from the posterior cut guide.

In Example 16, a method for preparing a distal femur for an implant, the method. comprising: resecting a distal end of a femur to produce a resected surface; positioning an integrated instrument against the resected surface such that: a pair of shims engage posterior surfaces of medial and lateral condyles of the femur; and a pair of feet engage a superior portion of a tibia; adjusting a distance between the pair of shims and the pair of feet; adjusting a pivot angle between the pair of tabs and the pair of feet; and determining a posterior offset based on the distance and pivot angle.

Example 17 can include, or can optionally be combined with the subject matter of Example 16, to optionally include that the integrated instrument is further positioned against the resected surface such that: posterior and anterior cut guides engage posterior and anterior portions of the resected femur; and a posterior and anterior chamfer cut guide engages the resected surface.

Example 18 can include, or can optionally be combined with the subject matter of Example 17, to optionally include adjusting a distance between the anterior and posterior cut guides.

Example 19 can include, or can optionally be combined with the subject matter of Examples 17 and 18, to optionally include affixing the cut guides to the resected femur; and removing the pair of shims and the pair of feet from the cut guides.

Example 20 can include, or can optionally be combined with the subject matter of Examples 16, 17, 18 and 19, to optionally include resecting an anterior portion of the distal end of the femur to form an anterior surface; resecting a posterior portion of the distal end of the femur to form a posterior surface; resecting a chamfer between the resected surface and the anterior surface; and resecting a chamfer between the resected surface and the posterior surface.

These and other examples and features of the present systems and methods will be set forth in part in the following Detailed Description. This Overview is intended to provide non-limiting examples of the present subject matter it is not intended to provide an exclusive or exhaustive explanation. The Detailed Description below is included to provide further information about the present systems and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
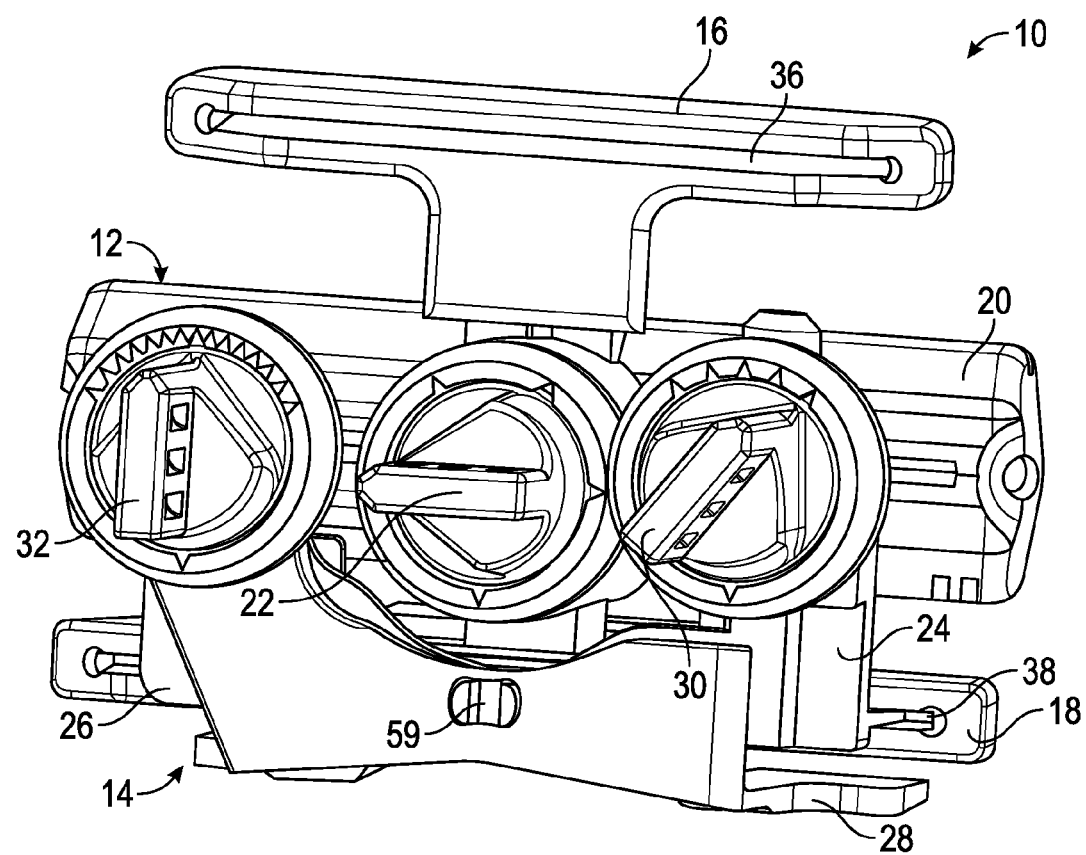
FIG. 1 is a perspective view of an integrated instrument for arthroplasty planning, in accordance with at least one example of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

Figure 2:
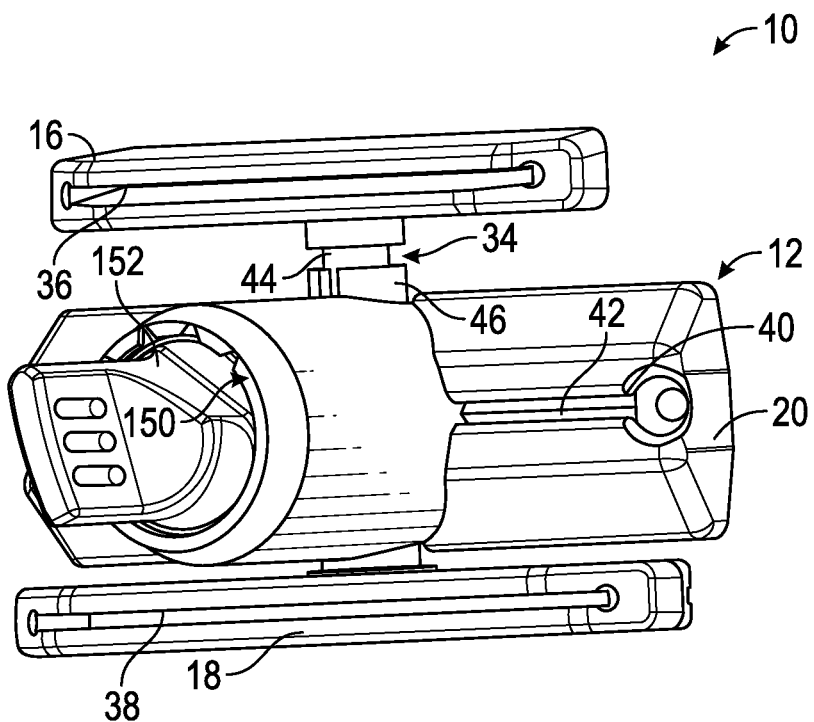
FIG. 2 is an exploded view of the integrated instrument of FIG. 1 showing an adjustable 4-in-1 cut block and a portion of an adjustable sizer, in accordance with at least one example of the present disclosure.
Figure 2:
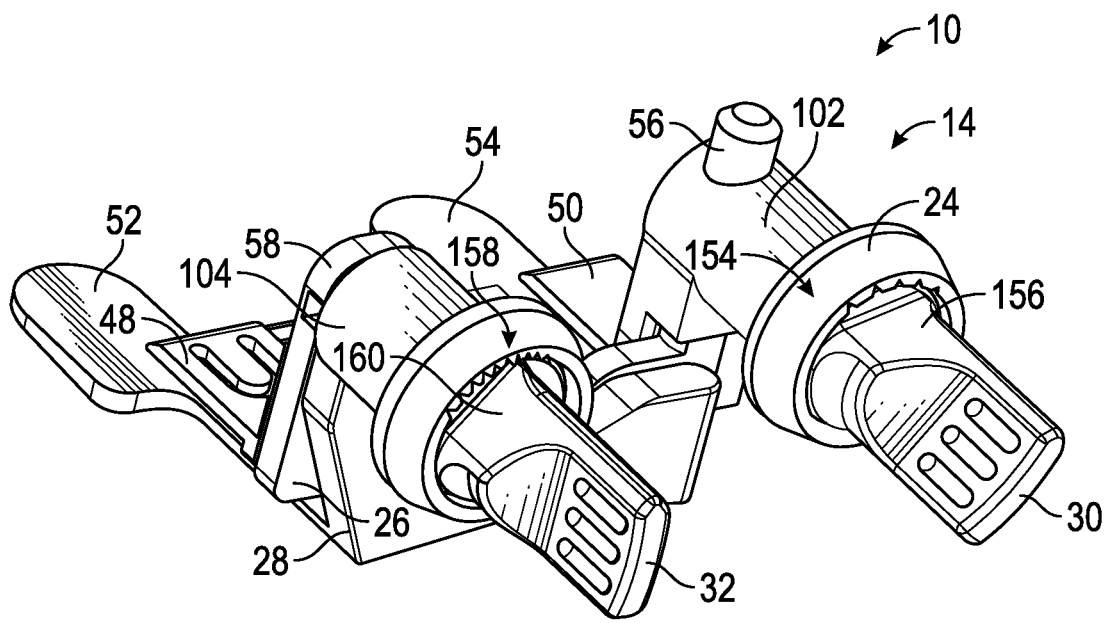

FIG. 1 is a perspective view of integrated instrument 10 for arthroplasty planning having adjustable 4-in-1 cut block 12 and a portion of adjustable sizer 14. FIG. 2 is an exploded view of integrated instrument 10 of FIG. 1 showing adjustable 4-in-1 cut block 12 and adjustable sizer 14. FIGS. 1 and 2 are discussed concurrently. Adjustable sizer 14 is typically used with a stylus that provides a contact for an anterior portion of the femur, as discussed below with reference to FIG. 8, while feet 52 and 54 (FIG. 3) provide contact with a posterior portion of the femur. Adjustable sizer 14 can be used with an anterior or posterior stylus.

Adjustable 4-in 1 cut block 12 can include anterior cut guide 16, posterior cut guide 18, chamfer block 20 and first adjuster knob 22. Adjustable sizer 14 can include shim body 24, adjuster body 26, foot body 28, second adjuster knob 30 and third adjuster knob 32.

Anterior cut guide 16 and posterior cut guide 18 can be configured to adjust their relative positions about adjustable post 34 using first adjuster knob 22. Anterior cut guide 16 and posterior cut guide 18 can include anterior cut slot 36 and posterior cut slot 38, respectively. Chamfer block 20 can be mounted to adjustable post 34 and includes anterior chamfer slot 40 and posterior chamfer slot 42. Adjustable post 34 comprises anterior post 44 and posterior post 46.

Anterior and posterior cut slots 36 and 38 can be configured to align a cutting device, e.g. a saw blade, with anterior and posterior portions of femoral condyles to facilitate making anterior and posterior resections of the bone. Anterior and posterior chamfer slots 40 and 42 can be configured to align a cutting device, e.g. a saw blade, with anterior and posterior portions of femoral condyles to facilitate making chamfer resections between the anterior and posterior resections and a previously made distal femoral resection. As discussed in greater detail below with reference to FIGS. 3-7, first adjuster knob 22 can engage anterior post 44 and posterior post 46 of adjustable post 34 to control a distance between anterior cut guide 16 and posterior cut guide 18, which can be set relative to a fixed location located therebetween.

Second adjuster knob 30 can be configured to adjust the distance between shim body 24 and foot body 28 using adjuster body 26. Third adjuster knob 32 can be configured to adjust the angular relationship between shim body 24 and foot body 28 using adjuster body 26.

Shim body 24 can include medial shim 48 and lateral shim 50, which can be configured to be inserted into posterior cut slot 38. Foot body 28 can include medial foot 52 and lateral foot 55, which can be configured to engage a proximal end of a tibia or a spacer disposed thereon, as well as the posterior femur for relative position of the cuts to femoral anatomy. As discussed in greater detail below with reference to FIGS. 8-11, second adjuster knob 30 engages a notch in slide pin 56 to adjust the distance between shims 48 and 50 and feet 52 and 54, and third adjuster knob 32 can engage a slot in tab 58 to adjust the angular relationship between shims 48 and 50 and feet 52 and 54, such as at pivot point 59.

Figure 3:
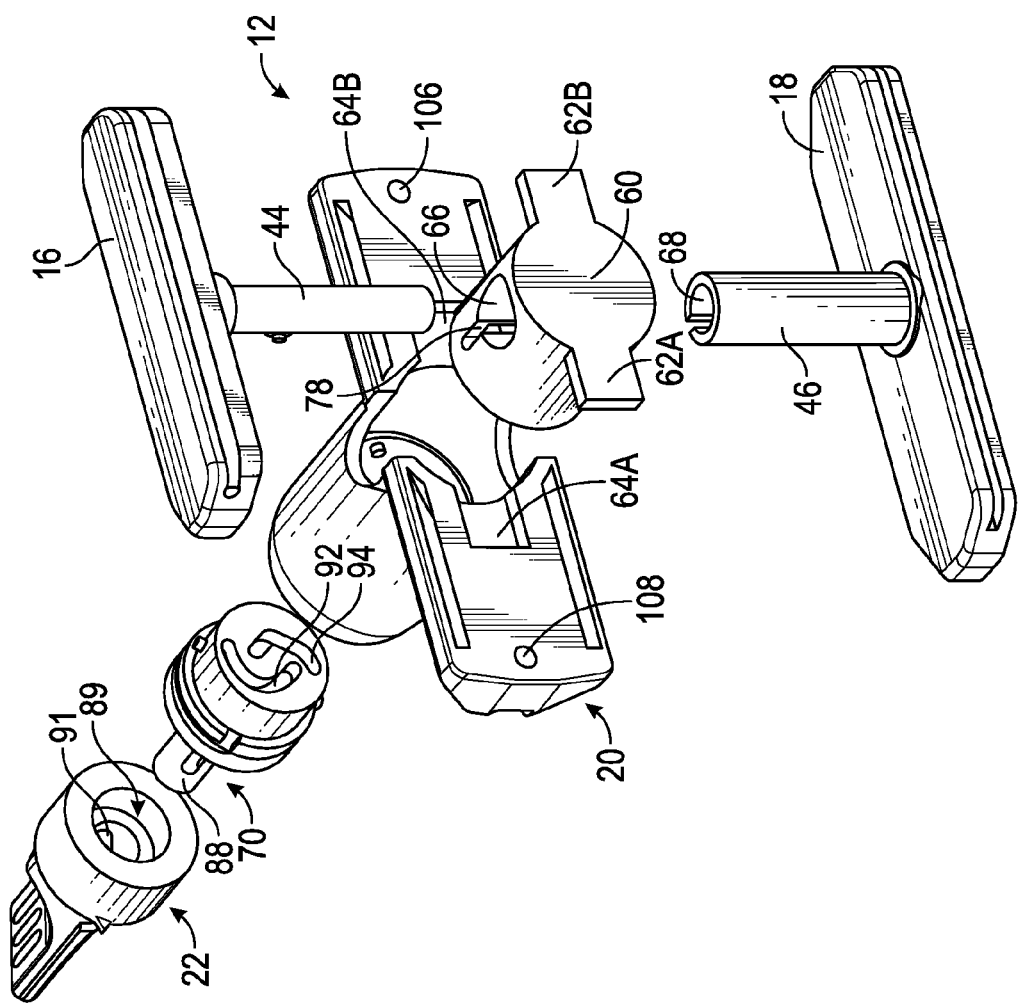
FIG. 3 is an exploded perspective view of the adjustable 4-in-1 cut block of FIG. 2 showing an anterior cut guide, a chamfer block, and a posterior cut guide connected to a main body, in accordance with at least one example of the present disclosure.
Figure 4:
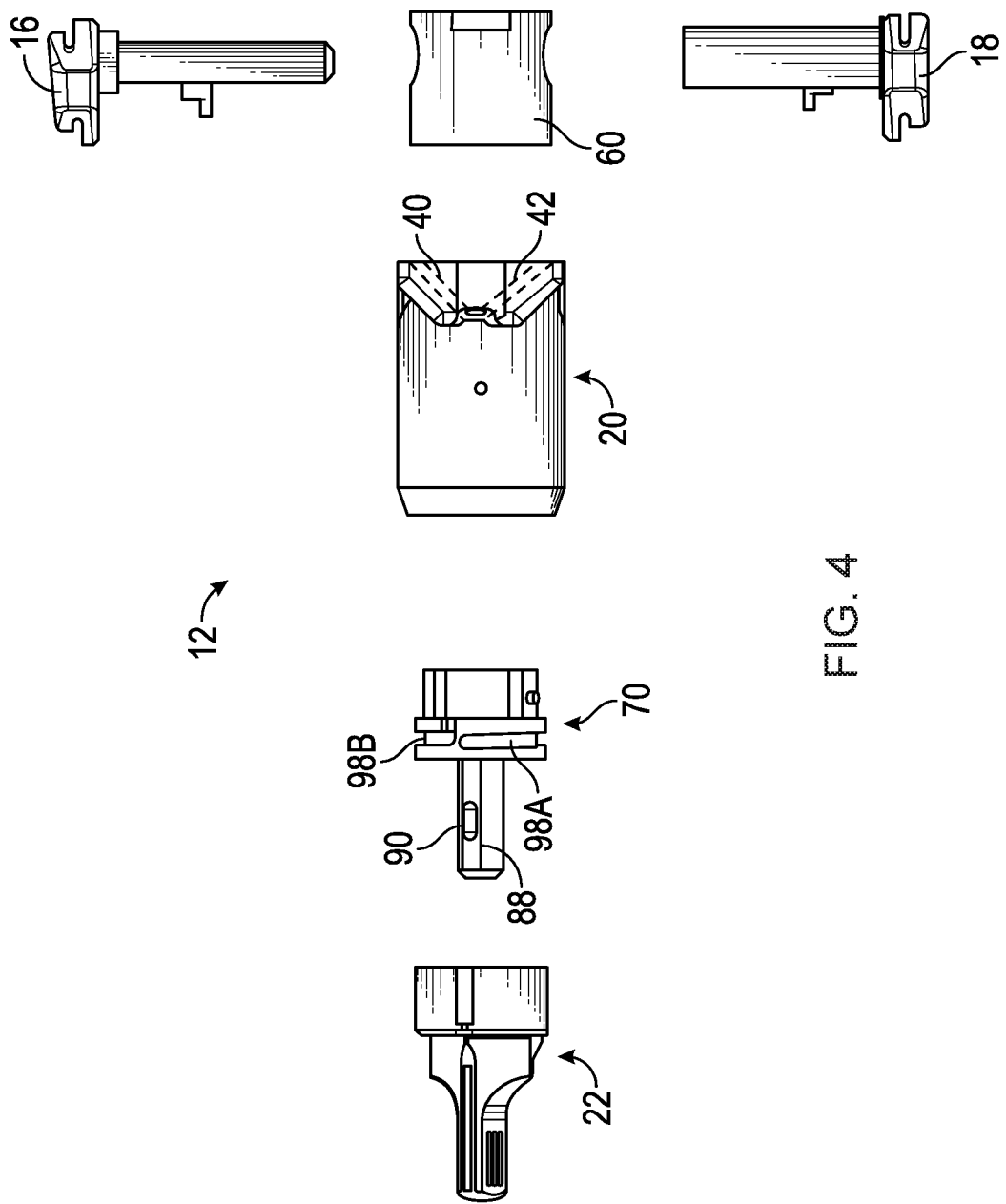
FIG. 4 is an exploded side view of the adjustable 4-in-1 cut block of FIG. 2 showing a first adjuster knob aligned with a drive pin and the main body, in accordance with at least one example of the present disclosure.

FIG. 3 is an exploded perspective view of the adjustable 4-in-1 cut block 12 of FIG. 2 showing anterior cut guide 16, chamfer block 20 and posterior cut guide 18 connected to main body 60. FIG. 4 is an exploded side view of adjustable 4-in-1 cut block 12 of FIG. 2 showing first adjuster knob 22 aligned with drive pin 70 and main body 60. FIGS. 3 and 4 are discussed concurrently.

Anterior cut guide 16, posterior cut guide 18 and chamfer block 20 can be mounted to main body 60. Main body 60 can act as a reference point from which movement of anterior cut guide 16, posterior cut guide 18 and chamfer block 20 is related. Main body 60 can include wings 62A and 62B that are fitted into sockets 64A and 64B in chamfer block 20 to prevent relative rotation therebetween. The specific size of wings 62A and 62B and sockets 64A and 64B, including width, depth and thickness, can vary in different examples of the device. Main body 60 can also include bore 66 into which posterior post 46 is inserted. Posterior post 46 can include bore 68 into which anterior post 44 is inserted to form adjustable post 34 (FIG. 2). Anterior chamfer slot 40 and posterior chamfer slot 42 can be seen in phantom extending through chamfer block 20 in FIG. 4.

Figure 5:
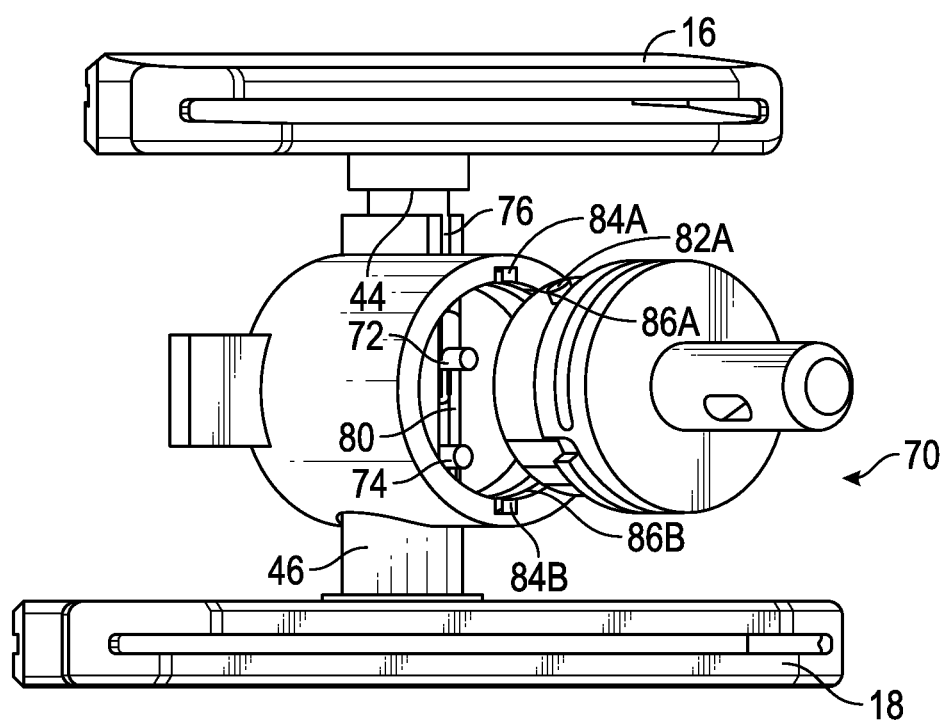
FIG. 5 is a partial assembled view of the adjustable 4-in-1 cut block of FIG. 2 with the chamfer block and first adjuster knob removed from the drive pin to show first and second posts of the anterior and posterior cut guides, respectively, disposed within the main body to form an adjustable post, in accordance with at least one example of the present disclosure.
Figure 6:
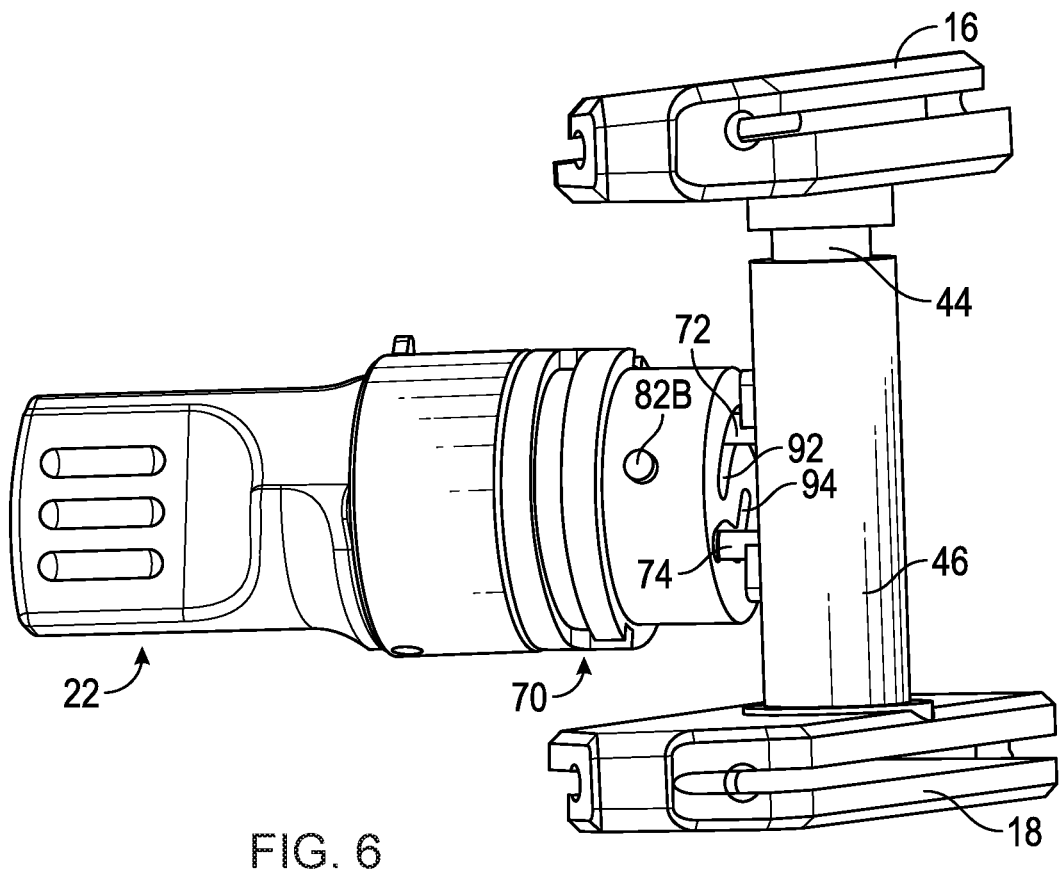
FIG. 6 is a partial assembled view of the adjustable 4-in-1 cut block of FIG. 2 with the main body removed to show fingers of the first and second posts disposed within slots of the drive pin, in accordance with at least one example of the present disclosure.
Figure 7:
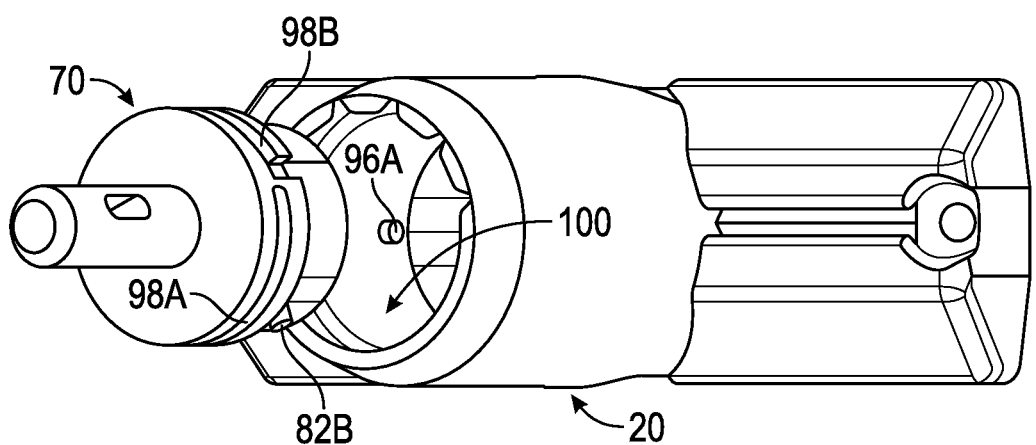
FIG. 7 is a perspective view of the drive pin exploded from the chamfer block to show an alignment tab of the chamfer block and alignment slots of the drive pin, in accordance with at least one example of the present disclosure.

First adjuster knob 22 can be connected to drive pin 70, which passes through chamfer block 20 (as can be seen in FIG. 7) to be inserted into main body 60 (as can be seen in FIG. 5) to couple with anterior post 44 and posterior post 46 (as can be seen in FIG. 6).

FIG. 5 is a partial assembled view of adjustable 4-in-1 cut block 12 of FIG. 2 with chamfer block 20 and first adjuster knob 22 removed from drive pin 70 to show posts 44 and 46 of anterior and posterior cut guides 16 and 18, respectively, disposed within main body 60 to form adjustable post 34. Anterior post 44 can include anterior finger 72, and posterior post 46 can include posterior finger 74.

Posterior post 46 can include cutout 76 to accommodate finger 72. Likewise, main body 60 can include cutout 78 (FIG. 3) to accommodate fingers 72 and finger 74. The cutouts of main body 60 can connect to slot 80 in which fingers 72 and 74 translate when actuated by drive pin 70.

Drive pin 70 can be inserted into main body 60 by aligning protrusion 82A with notch 84A that connects to channel 86A in main body 60. Main body 60 can also include notch 84B and channel 86B for mating with protrusion 82B (FIG. 6). Drive pin 70 can be coupled to first adjuster knob 22 (FIG. 4) via insertion of shaft 88 into complimentary bore 89 (FIG. 3) within knob 22. A pin or other fastener 91 (FIG. 3) can be inserted through knob 22 and hole 90 in shaft 88 to prevent relative rotational movement between drive pin 70 and knob 22. A spring, can be positioned around shaft 88 to bias knob 22 away from drive pin 70. Thus, rotation of knob 22 by an operator of instrument 10 can cause drive pin 70 to rotate, which in turn can cause posts 44 and 46 to be drawn toward or pushed away from each other while remaining proportionally spaced from main body 60.

FIG. 6 is a partial assembled view of adjustable 4-in-1 cut block 12 of FIG. 2 with chamfer block 20 removed to show fingers 72, 74 of posts 44, 46 disposed within slots 92, 94, respectively, of drive pin 70. FIG. 6 also shows protrusion 82B of drive pin 70.

Drive pin 70 can operate as a cam wheel to produce movement of posts 44 and 46. As can be seen in FIG. 3, slots 92 and 94 are irregularly shaped such that rotation about a central axis extending through shaft 88 of drive pin 70 can cause linear movement of fingers 72 and 74. Slots 92 and 94 can be differently shaped to produce different rates of travel of posts 44 and 46.

As drive pin 70 rotates, protrusions 82A and 82B can retain drive pin 70 within channels 86A and 86B of main body 60. Drive pin 70 can be retained within chamfer block 20 using a similar protrusion and channel connection.

FIG. 7 is a perspective view of drive pin 70 exploded from chamfer block 20 to show alignment tab 96A of chamfer block 20 and alignment slots 98A and 98B of drive pin 70. Drive pin 70 can be inserted into chamber 100 of chamfer block 20 so that alignment tab 96A engages alignment slot 98A. Likewise, alignment tab 96B (not shown) opposite alignment tab 96A within chamber 100 can engage alignment slot 98B. Slots 98A and 98B can allow rotation of pin 70 within chamber 100, but can also control axial movement when fully engaged. As can be seen in FIG. 4, slots 98A and 98B vary their distance from the ends of pin 70 to allow chamfer block 20 to move relative to main body 60, while protrusions 82 keep pin 70 fixed relative to main body 60. Furthermore, with pin 70 fully seated in chamfer block 20, knob 22 can be coupled to protrusions 82A and 82B to further prevent axial displacement of drive pin 70 from chamber 100. In other examples, drive pin 70 can include a single slot and chamfer block 20 can include a single alignment tab. For example, only one of slots 98A and 98B can be used with one of alignment tabs 96A and 96B. In such examples, drive pin 70 can be configured to provide more than one-hundred-eighty degrees of adjustment. For example, the slot can be configured to extend three-hundred-sixty degrees around chamber 100 to allow drive pin 70 full rotational capabilities, if desired. A single slot and a single tab can be configured to assemble in only one way so as to also provide fool-proofing of the assembly of adjustable 4-in-1 cut block 12.

With reference to FIG. 2, as will be discussed in greater detail later, rotation of knob 22 can extend and retract anterior cut guide 16 and posterior cut guide 18 from chamfer block 20. In one example, right-hand rotation of knob 22 can push anterior cut guide 16 and posterior cut guide 18 away from chamfer block 20 to allow for wider anterior and posterior resectioning of larger femurs, while left-hand rotation of knob 22 can pull anterior cut guide 16 and posterior cut guide 18 closer to chamfer block 20 to allow for narrower anterior and posterior resectioning of smaller femurs. Once anterior cut guide 16 and posterior cut guide 18 are positioned in a desired location, anterior chamfer slot 40 and posterior chamfer slot 42 are additionally properly positioned, e.g. between anterior cut guide 16 and posterior cut guide 18, to allow for chamfer resectioning of the femur.

Figure 8:
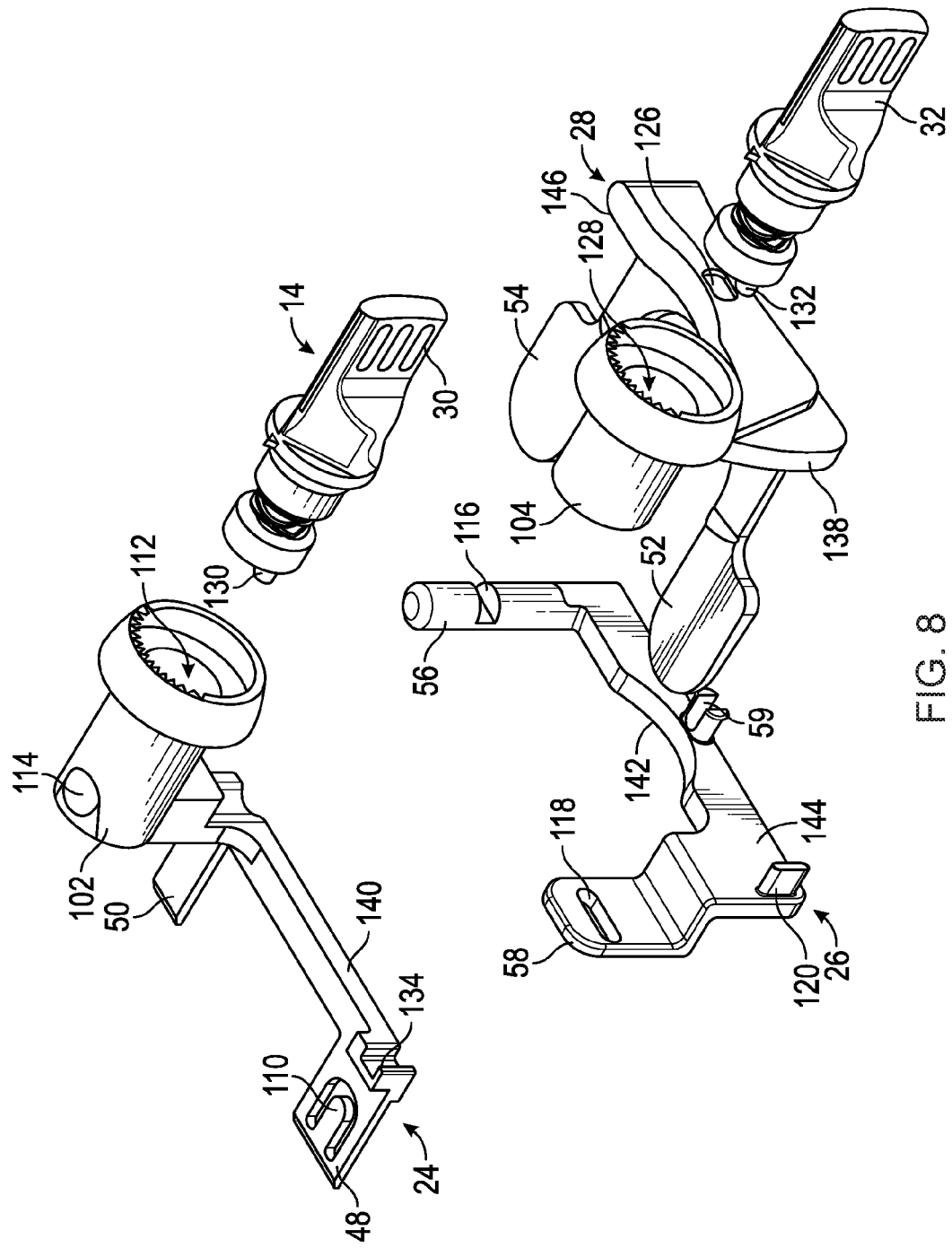
FIG. 8 is an exploded perspective view of a portion of the adjustable sizer of FIG. 2 showing a shim body, an adjuster body and a foot body, in accordance with at least one example of the present disclosure, in accordance with at least one example of the present disclosure.
Figure 9:
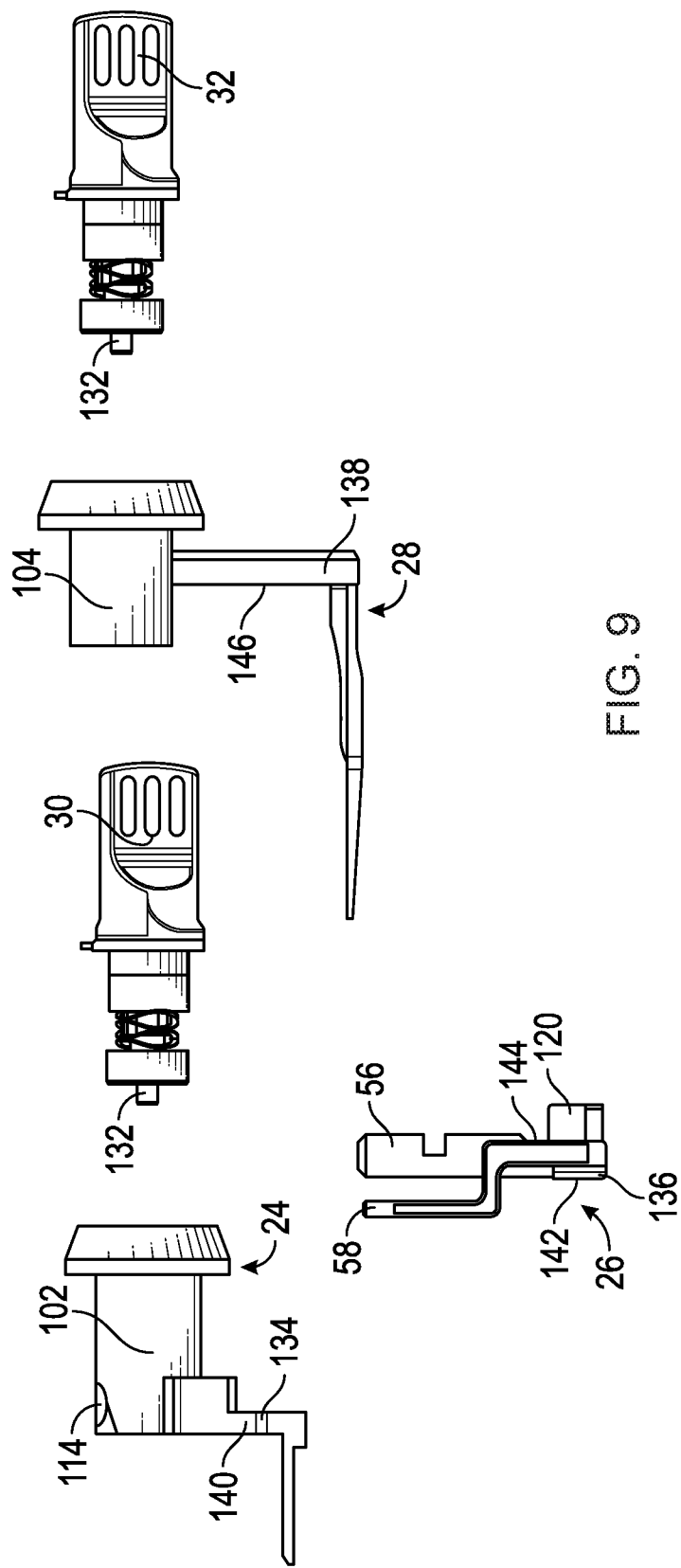
FIG. 9 is an exploded side view of a portion of the adjustable sizer of FIG. 2 showing alignment of a second adjuster knob with a second collar in the foot body, and alignment of a third adjuster knob with a third collar in the shim body, in accordance with at least one example of the present disclosure.

FIG. 8 is an exploded perspective view of adjustable sizer 14 of FIG. 2 showing shim body 24, adjuster body 26 and foot body 28, as well as second adjuster knob 30 and third adjuster knob 32. FIG. 9 is an exploded side view of adjustable sizer 14 of FIG. 2 showing alignment of second adjuster knob 30 with collar 102 in foot body 28, and alignment of third adjuster knob 32 with collar 104 in shim body 24.

Shim body 24 can also include medial shim 48, lateral shim 50, retention tab 110, knob chamber 112 and pin bore 114. Adjuster body 26 can also include slide pin 56, tab 58, pivot point 59, notch 116, slot 118 and stop 120. Foot body 28 can also include medial foot 52, lateral foot 54, pivot hole 126 and knob chamber 128. Second adjuster knob 30 can include finger 130, and third adjuster knob 32 can include finger 132.

Adjuster body 26 can be coupled to shim body 24 such as by inserting slide pin 56 into pin bore 114. Also, notch 134 on shim body 24 can receive tab 136 (FIG. 9) on adjuster body 26. As such, shim body 24 can be configured to translate relative to adjuster body 26 in a longitudinal or linear direction.

Foot body 28 can be coupled to adjuster body 26 such as by inserting pivot point 59 into pivot hole 126. Pivot point 59 can comprise a pair of opposing tabs with flanges that can flex toward each other to allow pivot hole 126 to pass over the flanges. Once foot body 28 is advanced to engagement with adjuster body 26 the tabs can spring back away from each other so that the flanges can prevent the tabs from passing out of pivot hole 126. As such, foot body 28 can be configured to pivot relative to adjuster body 26 and shim body 24 at pivot point 59. Stop 120 can engage wall 138 on foot body 28 to limit the amount of pivoting. As shown, pivot point 59 is centered and one of feet 48 and 50 can be used for a right or left knee. In other examples, pivot point 59 can be offset from the center such that adjustable sizer 14 can be side-specific. For example, a right-side specific device could have pivot point 59 offset closer to foot 54 and a left-side specific device could have pivot point 59 closer to foot 52. In yet other examples, offsetting of pivot point 59 could only move one of feet 48 and 50 relative to its respective shim, leaving the other foot and shim at a consistent distance. This last example could also result in a change in angle from only one condyle.

When fully assembled, face 140 of shim body 24 can abut face 142 of adjuster body 26, and face 144 of adjuster body 26 can abut face 146 of foot body 28.

Figure 10:
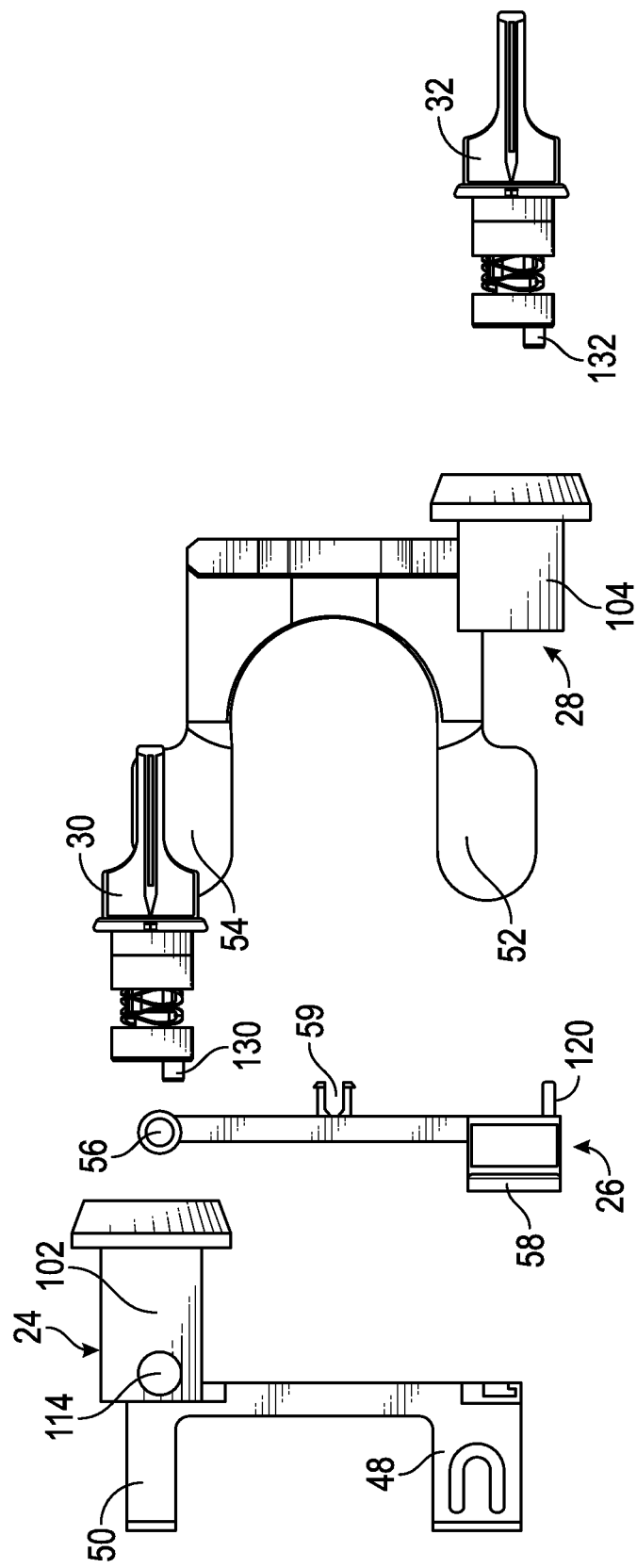
FIG. 10 is an exploded top view of a portion of the adjustable sizer of FIG. 2 showing the second adjuster knob aligned with a slide pin of the adjuster body, and the third adjuster knob aligned with a slot of the adjuster body, in accordance with at least one example of the present disclosure.
Figure 11:
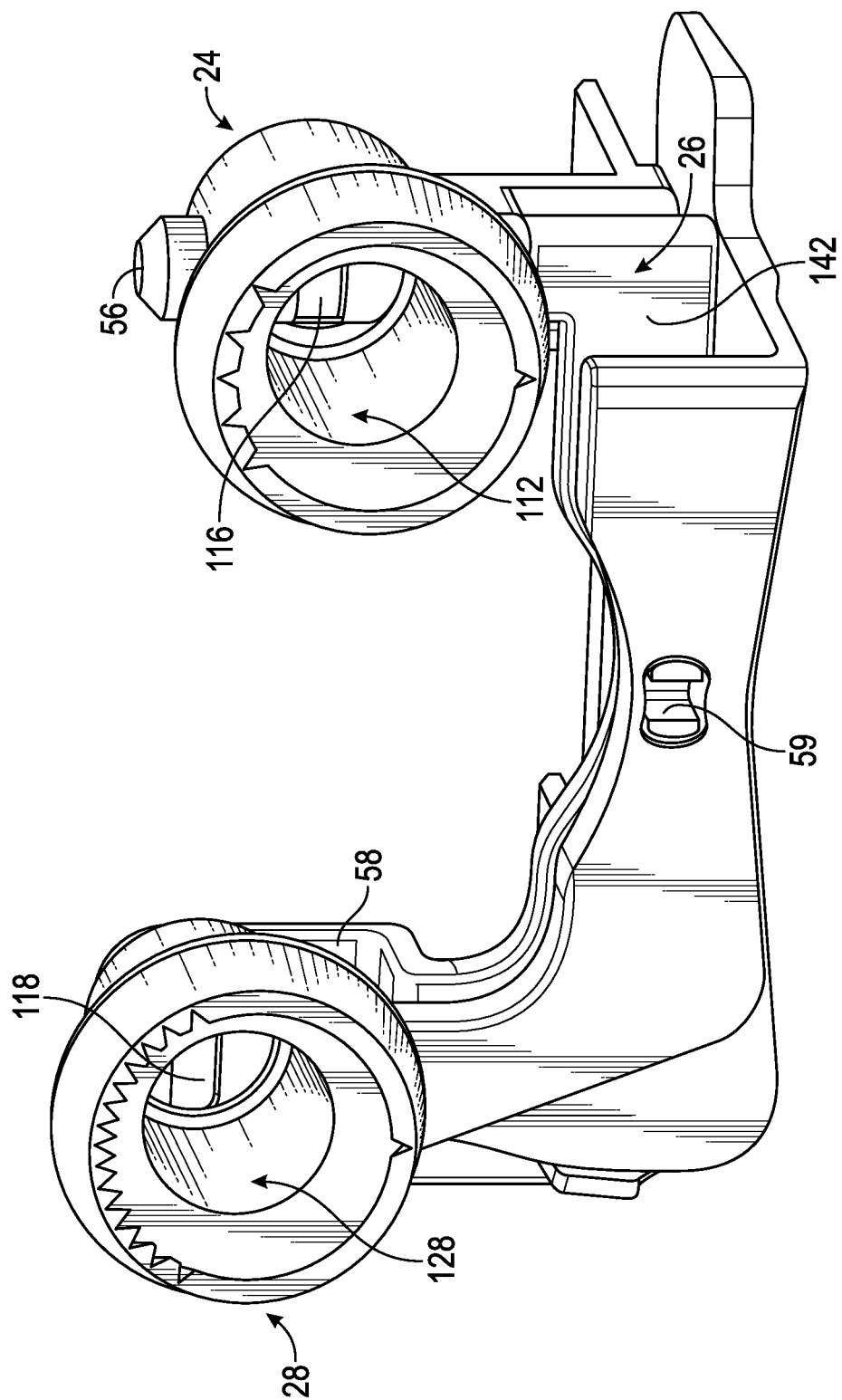
FIG. 11 is a partial assembled view of a portion of the adjustable sizer of FIG. 2 with the second and third adjuster knobs omitted to show a notch in the slide pin within the second collar and a slot in the adjuster body within the third collar, in accordance with at least one example of the present disclosure.

FIG. 10 is an exploded top view of adjustable sizer 14 of FIG. 2 showing second adjuster knob 30 aligned with slide pin 56 of adjuster body 26, and third adjuster knob 32 aligned with slot 118 of adjuster body 26. FIG. 11 is a partial assembled view of adjustable sizer 14 of FIG. 2 with second and third adjuster knobs 30 and 32 omitted to show notch 116 in slide pin 56 within second collar 102, and slot 118 in adjuster body 26 within third collar 104.

Second adjuster knob 30 can be inserted into knob chamber 112 such that finger 130 can be positioned in pin bore 114. As such, finger 130 can engage notch 116 in slide pin 56. As shown in FIG. 11, notch 116 is disposed adjacent knob chamber 112. When adjuster knob 30 is rotated, finger 130 can push against slide pin 56 in notch 116 to move shim body 26 up and down along slide pin 56. Due to confinement of slide pin 56 within pin bore 114, this can cause shims 48 and 50 to move away from or towards feet 52 and 54.

Third adjuster knob 32 can be inserted into knob chamber 128 such that finger 132 can be positioned in pin slot 118 (FIG. 8). As such, finger 132 can engage slot 118 in tab 58. As shown in FIG. 11, slot 118 is disposed adjacent knob chamber 128. When adjuster knob 32 is rotated, finger 132 can push against tab 58 in slot 118 to pivot foot body 28 relative to adjuster body 26 at pivot point 59. Due to the lack of constraint on foot body 28 other than that of pivot point 59, this can cause feet 52 and 54 to be angled relative to shims 48 and 50. For example, foot 52 can move toward shim 48, while foot 54 can move away from shim 50, and vice versa, due to constraint of movement of foot body 28 at pivot point 59.

Referring to FIG. 2, knobs 22, 30 and 32 can be configured to engage with notches in their respective housings in order to lock the knob into a position, which can correspond to a predetermined or known orientation of instrument 10. Chamfer block 20 can include notches 150 that can engage with point 152 of knob 22. Collar 102 can include notches 154 that can engage with point 156 of knob 30. Collar 104 can include notches 158 that can engage with point 160 of knob 32. Notches 150, 154 and 156 can correspond to know dimensions such that the size of the femur can be determined and appropriately sized or prosthetic components can be selected.

4-in-1 cut block 12 and adjustable sizer 14 can be used in conjunction with a surgical plan, either a pre-surgical plan or a plan developed intraoperatively, to size the femur of the patient to receive an artificial knee implant. Once the femur is initially sized, a 4-in-1 block can be selected. 4-in-1 cut block 12 can be selected and configured in different sizes to accommodate different sizes of patient femurs. Either before or after the 4-in-1 block is selected, a distal-most portion of the femur can be removed, including distal portions of the medial and lateral condyles. 4-in-1 cut block 12 can then be sized based on the surgical plan to fit the sized and resected femur by adjusting knob 22.

Adjustable sizer 14 can next be assembled. Adjuster sizer 14 can be pre-set to dimensions from the surgical plan or another setting. If a multi-piece sizer is used, an anterior stylus can be assembled to adjustable sizer 14. For example, a stylus as is described in U.S. Pat. No. 9,050,197 to Lorio et al., which is hereby incorporated by this reference in its entirety for all purposes, can be used with adjustable sizer 14. Next, adjustable sizer 14 can be assembled with the selected 4-in-1 cut block 12.

In one example, the stylus, adjustable sizer 14 and cut block 12 can be assembled together as one unit. In other examples, a surgeon could choose to assemble just two of the components, such as the stylus with adjustable sizer 14 or adjustable sizer 14 and cut block 12. In another example, cut block 12 can be assembled with a fixed (not adjustable) version of a foot. A fixed version of a foot is described in the aforementioned patent to Lorio et al.

Adjustable sizer 14 can be assembled to cut block 12 by insertion of shims 48 and 50 into posterior cut slot 38. In another example, cut block 12 can be provided with an additional slot for receiving shims 48 and 50 such that none of the cut slots are obstructed. For example, a dedicated shim slot could be provided just above or below posterior cut slot 38. Such a dedicated shim slot can be useful with implant systems that may not have consistent posterior or anterior resections and the separate attachment could allow feet 52 and 54 or the stylus to be one part for all the blocks.

Next, the assembled components can be placed on the distal femoral resection such that posterior feet 52 and 54 touch the posterior condyles and the anterior stylus references the anterior femoral cortex. In such a position, face 142 of adjuster body 26 can face the resected surface of the femur. The stylus may not fit at this time due to minor differences between the plan and the patient anatomy. The surgeon can decide to vary the components to evaluate fits.

The surgeon can change the size of 4-in-1 cut block 12 by adjusting knob 22, which can alter the gap between anterior cut guide 16 and posterior cut guide 18. The posterior gap between feet 52 and 54 and shims 48 and 50 can be adjusted by rotating knob 32. The posterior angle between feet 52 and 54 and shims 48 and 50 can be adjusted by moving knob 30. As discussed above, points 152, 156 and 160 of knobs 22, 30 and 32 can engage notches 150, 154 and 158, respectively, to dispose instrument 10 into known configurations that correspond to dimensions of various prosthetic components that can be used in the knee replacement procedure. Any one of or any combination of knobs 22, 30 and 32 can be adjusted to evaluate the anterior and posterior gaps and how the femoral cuts relate to the femoral landmarks, like the epicondylar axis, and other bone geometries, like the tibia. This allows the surgeon to evaluate various configurations without removing the components (e.g. cut block 12 and adjustable sizer 14), to fit the patient's anatomy.

Once the size and position is determined, cut block 12 can be pinned to the femur. In one example, pins can be inserted through bores 106 and 108 (FIG. 3) in chamfer block 20. Once pinned, the sizer 14 and the anterior stylus are removed and resections can be made thru slots 36, 38, 40 and 42.

After resections, the pins are removed from chamfer block 20 and 4-in-1 cut block 12 can be removed. This finishes resection of the distal femoral bone in preparation for trialing and any additional steps, such as drilling femoral component lug holes thru the trial femoral component and preparation of the posterior stabilized femoral box, can be taken to complete the procedure.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features may be grouped together to streamline the disclosure. This should not be interpreted as intending that an unclaimed disclosed feature is essential to any claim. Rather, inventive subject matter may lie in less than all features of a particular disclosed example. Thus, the follow- The claimed invention is:

1. An integrated instrument for arthroplasty planning comprising:
   a cutting block having an adjustable distance between an anterior cut guide and a posterior cut guide;
   a sizer mounted to the cutting block, the sizer comprising:
      medial and lateral posterior feet having an adjustable distance from one of the cut guides and an adjustable angular position relative to the one of the cut guides;
   an adjustable post coupling together the anterior cut guide and the posterior cut guide, the adjustable post comprising:
      first and second posts connected to the anterior cut guide and the posterior cut guide, respectively, and telescopically connected to each other; and
      first and second fingers extending from the first and second posts, respectively;
      wherein the first and second fingers are coupled to the first adjuster knob to push and pull the first and second posts away from and toward each other; and
   a first adjuster knob connected to the adjustable post to change the adjustable distance between the anterior cut guide and the posterior cut guide.

2. The integrated instrument of claim 1, further comprising:
   a chamfer block mounted to the adjustable post, the chamfer block comprising:
      an anterior chamfer cut guide; and
      a posterior chamfer cut guide;
   wherein the first adjuster knob additionally adjusts a distance of the chamfer block from the anterior and posterior cut guides.

3. The integrated instrument of claim 1, wherein the sizer is mounted to the cutting block via a pair of shims inserted into one of the cut guides.

4. The integrated instrument of claim 3, further comprising a shim body having the pair of shims.

5. The integrated instrument of claim 4, further comprising a foot body connecting the medial and lateral posterior feet, the foot body being connected to the shim body via an adjuster body.

6. The integrated instrument of claim 5, wherein the adjuster body is slidably connected to the shim body at a slide pin and pivotably connected to the foot body at a pivot point.

7. The integrated instrument of claim 6, further comprising:
   a second adjuster knob coupled to the sizer to adjust an anterior-posterior distance between the foot body and the shim body along the slide pin; and
   a third adjuster knob coupled to the sizer to adjust an angle between the foot body and the shim body.

8. An integrated instrument for arthroplasty planning comprising:
   a cutting guide comprising:
      an anterior cut guide;
      a posterior cut guide spaced from the anterior cut guide via an adjustable post; and
      a first adjuster connecting the anterior and posterior cut guides to adjust a space between the anterior and posterior cut guides at the adjustable post; and
   an anterior-posterior sizer connected to the cutting guide assembly, the anterior-posterior sizer comprising:
      a shim body having medial and lateral shims;
      a foot body having medial and lateral posterior feet disposed adjacent the medial and lateral shims, respectively;
      an adjuster body connecting the shim body and the foot body via a pivot point and a slide pin;
      a first adjuster for adjusting the medial and lateral posterior feet relative to each other at the slide pin; and
      a second adjuster for adjusting the medial and lateral posterior feet relative to each other at the pivot point.

9. The integrated instrument of claim 8, wherein the adjustable post comprises:
   first and second posts connected to the anterior cut guide and the posterior cut guide, respectively, and telescopically connected to each other; and
   first and second fingers extending from the first and second posts, respectively;
   wherein the first and second fingers are coupled to the first adjuster to push and pull the first and second posts away from and toward each other.

10. The integrated instrument of claim 8, further comprising:
    a chamfer block mounted to the adjustable post, the chamfer block comprising:
       an anterior chamfer cut guide slot; and
       a posterior chamfer cut guide slot;
    wherein the first adjuster additionally adjusts a distance of the chamfer block from the anterior and posterior cut guides.

11. The integrated instrument of claim 8, further comprising:
    a second adjuster knob coupled to the sizer to adjust an anterior-posterior distance between the foot body and the shim body along the slide pin; and
    a third adjuster knob coupled to the sizer to adjust an angle between the foot body and the shim body.

12. The integrated instrument of claim 8, wherein:
    the anterior cut guide and the posterior cut guide are disposed parallel to each other perpendicular to the adjustable post;
    the medial and lateral shims are disposed in a first plane positioned within the posterior cut guide; and
    the medial and lateral posterior feet are disposed in a second plane spaced from the posterior cut guide.

13. An integrated instrument for arthroplasty planning comprising:
    a cutting block having an adjustable distance between an anterior cut guide and a posterior cut guide;
    a shim body having a pair of shims;
    a sizer mounted to the cutting block via the pair of shims inserted into one of the cut guides, the sizer comprising:
       medial and lateral posterior feet having an adjustable distance from one of the cut guides and an adjustable angular position relative to the one of the cut guides; and a foot body connecting the medial and lateral posterior feet, the foot body being connected to the shim body via an adjuster body, wherein the adjuster body is slidably connected to the shim body at a slide pin and pivotably connected to the foot body at a pivot point.

14. The integrated instrument of claim 13, further comprising:
a second adjuster knob coupled to the sizer to adjust an anterior-posterior distance between the foot body and the shim body along the slide pin; and
a third adjuster knob coupled to the sizer to adjust an angle between the foot body and the shim body.

15. The integrated instrument of claim 13, wherein the anterior cut guide and the posterior cut guide are coupled together at an adjustable post.

16. The integrated instrument of claim 15, further comprising:
a first adjuster knob connected to the adjustable post to change the adjustable distance between the anterior cut guide and the posterior cut guide.

17. The integrated instrument of claim 16, wherein the adjustable post comprises:
first and second posts connected to the anterior cut guide and the posterior cut guide, respectively, and telescopically connected to each other; and
first and second fingers extending from the first and second posts, respectively;
wherein the first and second fingers are coupled to the first adjuster knob to push and pull the first and second posts away from and toward each other.

18. The integrated instrument of claim 16, further comprising:
a chamfer block mounted to the adjustable post, the chamfer block comprising:
an anterior chamfer cut guide; and
a posterior chamfer cut guide;
wherein the first adjuster knob additionally adjusts a distance of the chamfer block from the anterior and posterior cut guides.

* * * * *